United States Patent
Krill et al.

(10) Patent No.: US 6,417,409 B1
(45) Date of Patent: Jul. 9, 2002

(54) PROCESS FOR THE PRODUCTION OF 2,3,5-TRIMETHYLHYDROQUINONE DIESTERS

(75) Inventors: Steffen Krill, Speyer; Klaus Huthmacher, Geinhausen, both of (DE)

(73) Assignee: Degussa-Huls AG, Frankfurt am Main (DE)

( * ) Notice: Subject to any disclaimer, the term of this patent is extended or adjusted under 35 U.S.C. 154(b) by 0 days.

(21) Appl. No.: 09/502,229

(22) Filed: Feb. 11, 2000

(30) Foreign Application Priority Data

Feb. 11, 1999 (DE) .......................................... 199 05 685

(51) Int. Cl.⁷ .............................................. C07C 37/00
(52) U.S. Cl. ...................................... 568/772; 568/763
(58) Field of Search .................................. 568/772, 763

(56) References Cited

U.S. PATENT DOCUMENTS 4,247,720 A * 1/1981 Baudouin et al.
6,063,968 A * 5/2000 Hubner et al.

FOREIGN PATENT DOCUMENTS

| EP | 0 850 910 A1 | * 12/1996 |
| EP | 0 850 912 A1 | 7/1998 |

* cited by examiner

*Primary Examiner*—Paul J. Killos
*Assistant Examiner*—Hector M Reyes
(74) *Attorney, Agent, or Firm*—Pillsbury Winthrop LLP

(57) ABSTRACT

The invention relates to an improved process for the production of 2,3,5-trimethylhydroquinone diesters by rearrangement of 2,6,6-trimethyl-2-cyclohexene-1,4-dione (4-oxoisophorone, ketoisophorone) in the presence of a dissolved, acidic catalyst and an acylating agent, such as for example carboxylic anhydrides or carboxylic acid halides. The 2,3,5-trimethylhydroquinone diester can optionally then be saponified to give free 2,3,5-trimethylhydroquinone (TMHQ), which is a valuable building block in the synthesis of vitamin E.

21 Claims, No Drawings

PROCESS FOR THE PRODUCTION OF 2,3,5-TRIMETHYLHYDROQUINONE DIESTERS

CROSS-REFERENCE TO RELATED APPLICATION

This application is based on German Application DE 199 05 685.4, filed Feb. 11, 1999, the disclosure of which is incorporated in its entirety herein by reference.

FIELD OF THE INVENTION

The invention relates to an improved process for the production of 2,3,5-trimethylhydroquinone diesters by rearrangement of 2,6,6-trimethyl-2-cyclohexene-1,4-dione (4-oxoisophorone, ketoisophorone) in the presence of a dissolved, acidic catalyst and an acylating agent, such as, for example, carboxylic anhydrides or carboxylic acid halides. The 2,3,5-trimethylhydroquinone diester can thereafter, optionally, be saponified to give free 2,3,5-trimethylhydroquinone (TMHQ), which is a valuable building block in the synthesis of vitamin E.

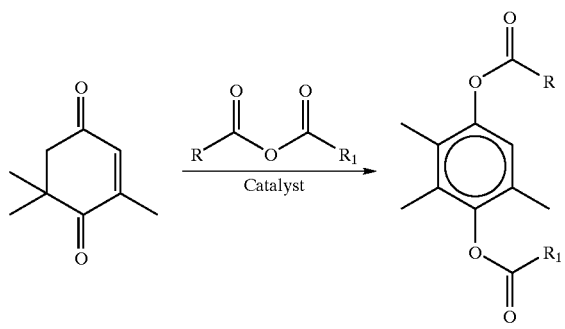

BACKGROUND OF THE INVENTION 2,3,5-Trimethylhydroquinone diesters and the corresponding TMHQ are important intermediates which are used in the production of vitamin E and vitamin E acetate. In addition to the known production process based on aromatic starting materials, 2,3,5-trimethylhydroquinone can be produced from a non-aromatic compound, 2,6,6-trimethyl-2-cyclohexene-1,4-dione, by rearrangement under acylating conditions and subsequent hydrolysis.

In patent specification DE 26 46 172 C2, a process is described in which 2,6,6-trimethyl-2-cyclohexene-1,4-dione is rearranged directly to trimethylhydroquinone in the vapor phase at a high temperature in contact with an acidic catalyst. However, the yield in this process is only low (50% with 30% conversion). If the aromatization of 2,6,6-trimethyl-2-cyclohexene-1,4-dione is carried out in the presence of an acylating agent, trimethylhydroquinone diesters are obtained which lead to trimethylhydroquinone by subsequent hydrolysis.

According to Bull. Korean. Chem. Soc. 1991, 12, 253, for example, the rearrangement is performed in a 5% solution in acetic anhydride by adding five equivalents of concentrated sulfuric acid. However, trimethylhydroquinone diester is only obtained in a 30% yield in this process.

In another process according to DE-OS 2 149 159, 2,6,6-trimethyl-2-cyclohexene-1,4-dione can be converted in the presence of acetic anhydride in a rearrangement catalyzed by protonic or Lewis acids to trimethylhydroquinone diacetate which is then saponified to trimethylhydroquinone.

Although by this method yields and conversions of ketoisophorone are is moderate to good (maximum 66% TMHQ yield, based on ketoisophorone used), large quantities of strong acids (up to 150 mole % based on ketoisophorone) and large excesses of acetic anhydride (5–10 moles $Ac_2O$/1 mole ketoisophorone) are used, which makes the process unattractive from an industrial point of view.

According to a more recent process (DE-OS 196 27 977), ketoisophorone is converted to the diester in the presence of only a double stoichiometric acetic anhydride equivalent with homogeneously dissolved super acids ($H_0 < -11.9$) as catalysts in the liquid phase. Particularly high selectivities are achieved with trifluoromethanesulfonic acid, chlorosulfonic acid and oleum of various $SO_3$ concentrations. A disadvantage of this process is the use of the above catalysts, the corrosive nature of which causes considerable material problems. The use of trifluoromethanesulfonic acid as catalyst is expensive and difficult, as this acid is complicated to handle and the reagent can only be partly recycled.

SUMMARY OF THE INVENTION

An object of the invention is to provide an improved process for the production of 2,6,6-trimethyl-2-cyclohexene-1,4-dione diesters, which, in particular, proceeds using an easily handled, economical catalyst. The corresponding hydroquinones can optionally be obtained from the esters by hydrolysis.

The invention provides a process for the production of trimethylhydroquinone diesters,

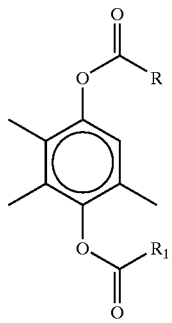

wherein R, $R_1$ are the same or different, by reacting 2,6,6-trimethyl-2-cyclohexene-1,4-dione(ketoisophorone or KIP)

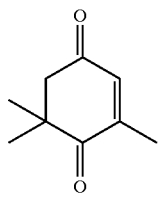

with an acylating agent in the presence of catalytic quantities of a protonic acid, which is characterized in that orthoboric acid and/or boron oxide on the one hand and one or more carboxylic acid(s), selected from the group of hydroxycarboxylic acids, di- or tricarboxylic acids, which optionally also contain hydroxy groups, on the other hand, are used.

This combined catalyst system is extraordinarily economical and is also easy to handle.

At the same time, yields and selectivities can be regarded as equivalent to those known from the prior art.

The activity of the catalyst system is based on a catalyst species formed in situ from the boron-containing compound and the carboxylic acids, the $pK_S$ value of which is lower than the $pK_S$ value of boric acid.

This catalyst combination is preferably used in a quantity of 0.1 to 10 mole %, based on the ketoisophorone used. It is present in the reaction mixture in dissolved form.

Many different boron compounds can be used as the boric acid derivative, especially boric acid triesters, boron oxides and boric acid, boric acid being used as the particularly preferred catalyst. Various oligofunctional compounds which react with boric acid derivatives, increasing the co-ordination sphere of boron, to form stable, complex boric acids, the acidic strength of which is stronger than that of the corresponding free boric acid, can be used as co-catalyst.

The ratio of boron component to co-catalyst can be varied within ranges between 1:1 and 1:10 (molar ratio), a ratio of 1:2 being particularly preferred in the case of bifunctional co-catalysts. The active catalyst species is formed in situ by reaction of the binary catalyst system of boric acid derivative and the co-catalyst in the presence of the acylating agent.

In particular, hydroxy acids of the general formula

$$R_2\text{---}CO_2H \qquad (I),$$

in which:

$R_2$ represents aryl, especially phenylene, naphthyl, each substituted by OH, HO—$(CH_2)_q$—, $CH_3(CHOH)_n(CH_2)_m$—, where m is an integer from 0 to 20, preferably 0 to 8, and n: an integer from 1 to 5, especially 1 to 4, q: an integer from 1 to 6 are designated as co-catalysts.

The particularly suitable hydroxycarboxylic acids include glycolic acid, lactic acid, mandelic acid, tartaric acid (regardless of the configuration), citric acid, especially salicylic acid or acetylsalicylic acid, but also hydroxyl group-containing amino acids such as serine or threonine and aldonic acid.

Dicarboxylic acids of the general formula

$$HO_2C\text{---}R_3\text{---}CO_2H \qquad (II),$$

in which:

$R_3$ represents aryl, especially phenylene, naphthyl, $(CH_2)_m$, wherein $m$ has the same meaning as above, or $(CH_2)_m(CHX)_r$, wherein r represents an integer from 1 to 5, and X is OH,H or $(CH_2)_p$—$(CX)(COOH)$—$(CH_2)_p$ with $p$=1 to 3 or alkenyl having $C_2$ to $C_6$, are also preferably used.

Oxalic acid, malonic acid, malic acid, succinic acid, glutaric acid, adipic acid, pimelic acid, suberic acid, azelaic acid, sebacic acid, especially oxalic acid, and aromatic dicarboxylic acids such as phthalic acid, isophthalic acid and terephthalic acid and 2,6-naphthalene-carboxylic acid or tricarboxylic acids such as trimesic acid or citric acid, and unsaturated dicarboxylic acids such as fumaric acid and maleic acid, but also polyhydroxydicarboxylic acids, are particularly suitable.

As acylating agent, compounds of the general formula:

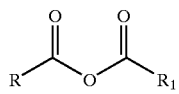

are preferably used, in which:

R, $R_1$, are the same or different and represent an optionally substituted, aliphatic, alicyclic $C_1$ to $C_{20}$ group, especially an aliphatic $C_2$ to $C_4$ group, or an aryl group, preferably phenylene.

The anhydride of acetic acid is particularly suitable.

Other suitable anhydrides are those of propionic acid, butyric acid, isobutyric acid, cyclohexane-carboxylic acid or benzoic acid.

The anhydrides of chloroacetic acid, trihaloacetic acid or trifluoromethansulfonic acid can also be used, even if they are not preferred.

The ratio between ketoisophorone and acylating agent can be varied within broad ranges, but a KIP/acylating agent ratio of 1:2 to 1:3 is particularly preferred. Other acylating reagents such as carboxylic acid halides, especially chlorides, enol esters and diketene corresponding to the above-mentioned anhydrides, can also be used as a synthesis equivalent and substitute for the preferably used acetic anhydride.

The process according to the invention can be carried out using inert organic solvents. The concentration of the reactants in the solvent has only an insignificant effect on the product profile of the reaction. It is particularly preferable to work without solvents, so that costly reprocessing operations or solvent recycling steps are avoided.

If the rearrangement takes place in the presence of organic solvents, suitable representative solvents are aliphatic and cyclic esters, e.g. ethyl acetate, propyl acetate, isopropyl acetate and γ-butyrolactone; hydrocarbons, for example hexane, heptane, toluene and xylene; and ketones, for example isobutyl methyl ketone, diethyl ketone and isophorone.

The KIP rearrangement takes place at temperatures of between −80° and +150° C., a temperature range of between −30° and +50° C. being particularly preferred. At even higher temperatures, by-product formation increases at the expense of the trimethylhydroquinone ester.

In one embodiment of the process according to the invention, the trimethylhydroquinone diester formed is crystallized directly from the carboxylic acid formed during the reaction. However, it is also possible to perform the isolation by adding a suitable solvent after distilling off the free carboxylic acid.

In another embodiment, the TMHQ diacetate formed is saponified without isolation, by adding water to the raw rearrangement mixture. The same catalyst already used for the rearrangement of ketoisophorone can be used as the saponification catalyst. The free trimethylhydroquinone is isolated by a method which is known per se, by crystallization from a suitable medium.

Trimethylhydroquinone synthesis has thus been successfully raised to a technically achievable, economical level by the provision of a reasonable, readily accessible, easy to handle catalyst system based on a boric acid derivative and operation as a cyclic process with catalyst recycling.

The production of 2,3,5-trimethylhydroquinone diesters and 2,3,5-trimethylhydroquinone according to the invention has the following substantial advantages compared with the prior art.

The yields of 2,3,5-trimethylhydroquinone diesters and 2,3,5-trimethylhydroquinone are among the highest values that can be achieved with trifluoromethanesulfonic acid as catalyst, with a yield of up to 95%, based on the ketoisophorone used.

Compared with the super acids known from the prior art, the catalyst has substantial handling advantages in terms of dosing, toxicity and corrosive properties. Thus, the catalyst can be produced by simply stirring together the catalyst components before use, or it is formed in situ by successive addition of the components to the carboxylic anhydride.

EXAMPLES

Example 1

1 g (=5.32 mmol) of a catalyst mixture comprising boric acid and oxalic acid in a molar ratio of 1:2 is added at room temperature, with stirring, to a solution of 28.3 ml acetic anhydride (=0.3 mol). Assuming that the active catalyst species is a 1:2 mixture of the two components with the emission of 2 mole equivalents water, the active catalyst has a molecular weight of 187.86 g/mol. This corresponds to a quantity of catalyst of 6.62 wt. % or 5.32 mole % based on KIP used.

A rapid temperature increase to 50° C. occurs. Over a period of 20 min, 15.1 g 20 KIP (=0.1 mol) are then added dropwise to this solution and the heat evolved is retained using a water bath in such a way that the temperature is kept constant at 50° C. After a secondary reaction period of one hour, the mixture is poured onto iced water and the crystals are sucked off and washed with water. Analysis by gas chromatography (GC) shows a quantitative conversion; yield and selectivity of trimethylhydroquinone diacetate are 88.2%. According to GC, by-product formation is approx. 11.6% trimethylpyrocatechol diacetate, which can be separated off by crystallization.

Example 2

A mixture of 28.3 ml acetic anhydride (=0.3 mol) and 0.4 g of a catalyst mixture (=2.12 mmol) of boric acid and oxalic acid (molar ratio 1:2) is prepared at 30° C. This corresponds to a quantity of catalyst of 2.13 mole % and 2.63 wt. % based on KIP used. At 30° C., KIP is slowly added dropwise (15.2 g=0.1 mol), and the mixture is then worked up in the conventional manner. According to GC, yield and selectivity of the reaction are 90.7%, and by-product formation is 8.8%.

Example 3

The procedure set forth in example 1 is followed, reducing the quantity of catalyst based on KIP to 1.33 mole % (=0.25 g of a mixture of boric acid and oxalic acid in a ratio of 1:2) or 1.64 wt. %. Under these conditions, maintaining the same reaction times, the conversion is 39.7% and the TMHQ-DA selectivity is 85.6 %. Unreacted KIP can be recovered and separated from the product by means of appropriate technical operations such as distillation or extraction.

Example 4

Working with 5.32 mole % of a catalyst mixture of boric acid and oxalic acid in a molar ratio of 1:2, the reaction is carried out at 10 to 15° C., retaining the heat evolved during the dropwise addition of KIP in an iced water bath. Selectivity and yield of TMHQ-DA are 92.9% by this method; the yield of by-products is 6.9%.

What is claimed is:
1. A process for the production of trimethylhydroquinone diesters of the formula

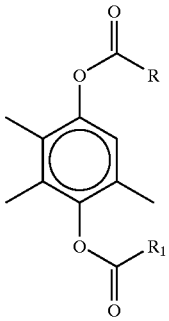

wherein R and $R_1$ may be identical or different moieties, and represent an optionally substituted aliphatic, alicyclic $C_1$ to $C_{20}$ group,
comprising reacting 2,6,6-trimethyl-2-cyclohexene-1,4-dione(ketoisophorone or KIP)

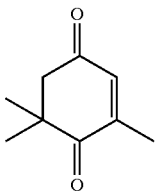

with an acylating agent in the presence of an acidic catalyst system comprising catalytic quantities of a protonic acid to form a trimethylhydroquinone diester,
wherein the protonic acid comprises at least one boron-containing member selected from the group consisting of orthoboric acid, boron oxide and boric acid triester and at least one carboxylic acid selected from the group consisting of hydroxycarboxylic acids, dicarboxylic acids and tricarboxylic acids, which optionally may also contain hydroxy groups.

2. The process according to claim 1, wherein the at least one carboxylic acid is a dicarboxylic acid of general formula $$HO_2C-R_3-CO_2H \qquad (II)$$

wherein $R_3$ represents a member selected from the group consisting of an aryl group, $(CH_2)_m$, and $(CH_2)_m(CHX)_r$,
wherein m represents an integer from 0 to 20, r represents an integer from 1 to 5 and X represents OH, H, $(CH_2)_p-(CX)(COOH)-(CH_2)_p$, or a $C_2-C_6$ alkenyl group and
wherein $_p$ represents a number from 1 to 3.

3. The process according to claim 2, wherein $R_3$ is a member selected from the group consisting of phenylene, naphthylene and $(CH_2)_m$.

4. The process according to claim 2, wherein $R_3$ is $(CH_2)_m$ or $(CH_2)_m(CHX)_r$ and m represents an integer from 0 to 4.

5. The process according to claim 1, wherein the at least one carboxylic acid comprises a hydroxy acid of general formula $$R_2-CO_2H \qquad (I)$$

wherein
R₂ represents an aryl compound substituted by at least one member selected from the group consisting of OH, HO—(CH₂)$_q$, and CH₃(CHOH)$_n$(CH₂)$_m$—, wherein
m represents an integer from 0 to 20,
n represents an integer from 1 to 5, and
q represents an integer from 1 to 6.

6. The process according to claim 5, wherein m represents an integer from 0 to 8.

7. The process according to claim 5, wherein n represents an integer from 1 to 4.

8. The process according to claim 1, wherein the at least one carboxylic acid comprises a hydroxyl group-containing amino acid.

9. The process according to claim 8, wherein the amino acid is serine or threonine.

10. The process according to claim 1, wherein the acidic catalyst system comprises a mixture of orthoboric acid and oxalic acid or salicylic acid.

11. The process according to claim 1, wherein the acidic catalyst system comprises a mixture of orthoboric acid and a member selected from the group consisting of oxalic acid, salicylic acid, tartaric acid and citric acid, in a molar ratio of 1:1 to 1:10.

12. The process according to claim 11, wherein the molar ratio is 1:2 to 1:5.

13. The process according to claim 1, wherein the acidic catalyst system comprises a mixture of one or more of the boron-containing members and one or more of the carboxylic acids in a quantity of 0.1 to 10 mole % based on the ketoisophorone used.

14. The process according to claim 1, wherein the acylating agent comprises an acylating agent of general formula

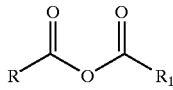

wherein:
R, R₁, are the same or different and represent an optionally substituted, aliphatic, alicyclic C₁ to C₂₀ group, or an aryl group.

15. The process according to claim 14, wherein the aliphatic group is a C₂ to C₄ aliphatic group.

16. The process according to claim 14, wherein the aryl group is a phenylene group.

17. The process according to claim 1, further comprising
optionally removing unreacted carboxylic acid anhydride and carboxylic acid by distillation, and
saponifying the trimethylhydroquinone diester without previous isolation, by adding at least one member selected from the group consisting of water and dilute acid, thereby forming trimethylhydroquinone.

18. The process according to claim 17, further comprising isolating the trimethylhydroquinone.

19. The process according to claim 14, wherein the acylating agent comprises a carboxylic acid chloride.

20. The process according to claim 1, wherein the at least one carboxylic acid comprises a compound of general formula (I)

wherein
R₂ represents an aryl compound substituted by at least one member selected from the group consisting of OH, HO—(CH₂)$_q$, and CH₃(CHOH)$_n$(CH₂)$_m$—, wherein
m represents an integer from 0 to 20,
n represents an integer from 1 to 5, and
q represents an integer from 1 to 6;
and a compound of general formula (II)

wherein R₃ represents a member selected from the group consisting of an aryl group, (CH₂)$_m$, and (CH₂)$_m$(CHX)$_r$,
wherein m represents an integer from 0 to 20, r represents an integer from 1 to 5 and X represents OH, H, (CH₂)$_P$—(CX)(COOH)—(CH₂)$_P$, or a C₂–C₆ alkenyl group and
wherein $p$ represents a number from 1 to 3.

21. The process according to claim 1, further comprising:
continuously separating catalytically active acids of the acidic catalyst system by extraction with a polar solvent, and
reprocessing the catalytically active acids for re-use.

* * * * *